United States Patent
Pflum

(10) Patent No.: US 8,226,722 B2
(45) Date of Patent: Jul. 24, 2012

(54) SAC FOR USE IN SPINAL SURGERY

(76) Inventor: Francis Pflum, Middletown, NJ (US)

( * ) Notice: Subject to any disclaimer, the term of this patent is extended or adjusted under 35 U.S.C. 154(b) by 388 days.

(21) Appl. No.: 11/450,600

(22) Filed: Jun. 8, 2006

(65) Prior Publication Data

US 2007/0299523 A1 Dec. 27, 2007

(51) Int. Cl.
*A61F 2/44* (2006.01)
(52) U.S. Cl. ................................... 623/17.16
(58) Field of Classification Search ..... 623/17.11–17.16
See application file for complete search history.

(56) References Cited

U.S. PATENT DOCUMENTS

| | | | |
|---|---|---|---|
| 4,349,921 A | 9/1982 | Kuntz | |
| 5,397,364 A | 3/1995 | Kozak et al. | |
| 5,514,180 A * | 5/1996 | Heggeness et al. | 623/17.16 |
| 5,549,679 A | 8/1996 | Kuslich | |
| 5,571,189 A | 11/1996 | Kuslich | |
| 5,609,635 A | 3/1997 | Michelson | |
| 5,645,598 A | 7/1997 | Brosnahan, III | |
| 5,700,291 A | 12/1997 | Kuslich et al. | |
| 5,702,449 A | 12/1997 | McKay | |
| 5,888,223 A | 3/1999 | Bray, Jr. | |
| 6,241,770 B1 | 6/2001 | Michelson | |
| 6,332,894 B1 | 12/2001 | Stalcup et al. | |
| 6,419,704 B1 * | 7/2002 | Ferree | 623/17.12 |
| 6,582,467 B1 * | 6/2003 | Teitelbaum et al. | 623/17.11 |
| 6,632,235 B2 | 10/2003 | Weikel et al. | |
| 6,800,245 B1 | 10/2004 | Erbe et al. | |
| 6,835,206 B2 | 12/2004 | Jackson | |
| 6,958,077 B2 * | 10/2005 | Suddaby | 623/17.11 |
| 6,969,405 B2 | 11/2005 | Suddaby | |
| 7,001,431 B2 * | 2/2006 | Bao et al. | 623/17.12 |
| 7,220,282 B2 | 5/2007 | Kuslich | |
| 7,226,481 B2 | 6/2007 | Kuslich | |
| 7,351,244 B2 | 4/2008 | Hamada | |
| 7,399,739 B2 | 7/2008 | Shimp | |
| 2002/0068974 A1 * | 6/2002 | Kuslich et al. | 623/17.11 |
| 2002/0123750 A1 * | 9/2002 | Eisermann et al. | 606/69 |
| 2003/0069641 A1 | 4/2003 | Reuter et al. | |
| 2004/0073308 A1 | 4/2004 | Kuslich et al. | |

(Continued)

FOREIGN PATENT DOCUMENTS

WO    WO 95/31948    11/1995

(Continued)

OTHER PUBLICATIONS

International Search Report and Written Opinion for PCT/US2007/070602.

(Continued)

*Primary Examiner* — Kevin T Truong
*Assistant Examiner* — David Bates
(74) *Attorney, Agent, or Firm* — White & Case LLP

(57) ABSTRACT

A method for fusing spinal bone is provided. The method comprises placing a sac between two or more adjacent sections of the spine to be fused, and filling the sac with bone tissue. The surfaces of the sac abutting the sections of the spine comprise porous material for allowing bone to grow between the spine and the sac. Surfaces of the sac not abutting the sections of the spine are nonporous to bodily fluids and thereby prevent premature deterioration of the bone tissue inside the sac. A sac for fusing spinal bone and a kit comprising the sac are also provided.

41 Claims, 1 Drawing Sheet

U.S. PATENT DOCUMENTS

| | | | |
|---|---|---|---|
| 2004/0091462 A1 | 5/2004 | Lin et al. | |
| 2004/0230309 A1* | 11/2004 | DiMauro et al. | 623/17.12 |
| 2004/0267368 A1* | 12/2004 | Kuslich | 623/17.16 |
| 2005/0043798 A1* | 2/2005 | Eckman | 623/17.11 |
| 2005/0055094 A1* | 3/2005 | Kuslich | 623/17.11 |
| 2005/0216089 A1 | 9/2005 | Michelson | |
| 2006/0293749 A1* | 12/2006 | Hudgins et al. | 623/17.11 |
| 2007/0093822 A1 | 4/2007 | DuToit et al. | |
| 2007/0168031 A1* | 7/2007 | Hudgins et al. | 623/17.12 |
| 2007/0270950 A1 | 11/2007 | Trieu | |
| 2008/0086133 A1 | 4/2008 | Kuslich et al. | |

FOREIGN PATENT DOCUMENTS

| | | |
|---|---|---|
| WO | WO 03/07853 | 1/2003 |
| WO | WO 2004/041075 | 5/2004 |
| WO | WO-2007/146738 | 12/2007 |
| WO | WO 2008/08522 | 1/2008 |
| WO | WO 2008/063642 | 5/2008 |

OTHER PUBLICATIONS

Future of Spine Surgery "Beyond Total Disc", Replication Medical, Inc. Neudisc™, Viscogliosi Bros., LLC, 2004.

Pflum et al., "Arthroscopic Anterior Diskectomy of the Cervical Spine", Arthroscopy: The J. of Arthroscopic and Related Surgery, vol. 24, No. 5 (May 2008):pp. 612-614.

International Preliminary Examination Report for PCT/US2007/070602.

* cited by examiner

SAC FOR USE IN SPINAL SURGERY

FIELD OF THE INVENTION

The present invention is directed to the field of medical technology. More specifically, the present invention is directed to methods for reconstructing sections of the spine using an implantable sac containing bone tissue.

BACKGROUND OF THE INVENTION

Certain technological advances have recently been applied to previously-accepted medical treatments of maladies of the spine. These technological advances have significantly facilitated the treatment of these spinal difficulties.

Specifically, these new treatments involve the use of scopes placed into the spine and small porous bags filled with bone chips to treat fractures of the spine and to fuse individual bone segments of the spine together. These bags are porous to allow ingrowth from adjacent bone and thereby join the bone segments.

There are certain problems with these prior art bags of bone chips for treating spinal maladies. If the bag is placed in the disc space, the exposed pores on the sides of the bag may allow the passage of body fluids through the pores into the bag. These bodily fluids have the opportunity to digest, soften, and change the non-compressive strength of the bag, thereby causing premature collapse before bone fusion has completed.

There are also uncertainties regarding an optimum size of the bag to be used. For example, if a surgeon wishes to place the bag in the disc space, there are uncertainties regarding the desired size, shape, and height of the bag.

Finally, there are issues regarding optimum orientation of the bag in the area to be fused, and assessment of proper orientation in position.

U.S. Pat. No. 5,571,189 discloses an expandable, porous fabric implant or bag for insertion into the interior of a reamed out disc which is packed with material to stabilize the spinal segment. The fabric pores allow for tissue ingrowth through the implant. A drawback to this bag is that bodily fluids can enter the porous sides of the bag and thereby digest or partially digest inserted bone graft material before fusion has completed, and thereby potentially causing failure of the implant or graft.

SUMMARY OF THE INVENTION

The present invention addresses the above problems regarding the use of implantable bags for spinal fusion. An object of the invention is to facilitate the use, effectiveness, and safety of a sac comprising bone tissue which is implanted into a section of the spine of a patient.

A first aspect of the present invention provides for a method for fusing spinal bone. The method comprises placing a sac between two or more adjacent sections of the spine to be fused, and filling the sac with bone tissue.

The surfaces of the sac abutting the sections of the spine comprise porous material for allowing bone to grow between the spine and the sac. Surfaces of the sac not abutting the sections of the spine are nonporous to bodily fluids and thereby prevent premature deterioration of the bone tissue inside the sac. A porous sac material is to be considered as a substance that allows bone to grow through it. A non-porous sac material is to be considered as a substance that prevents a significant amount of bodily fluids from passing through and dissolving or deteriorating the bone fragments contained inside the sac.

Another aspect of the invention provides for a sac for fusing spinal bone. The sac has generally flat upper and lower surfaces and a peripheral surface between the upper and lower surfaces. The surfaces of the sac define an interior volume intended to be filled with bone tissue prior to placement in the spine. The upper and lower surfaces of the sac comprise porous material for allowing bone to grow between the spine and the sac, and the peripheral surface is nonporous to bodily fluids to prevent deterioration of the bone tissue inside the sac.

Another aspect of the invention provides for a kit for fusing spinal bone. The kit comprises the sac according to an aspect of the invention; and an apparatus for filling the sac. The sac is filled with bone tissue and implanted into a section of a patient's spine.

DETAILED DESCRIPTION

Figure 1:
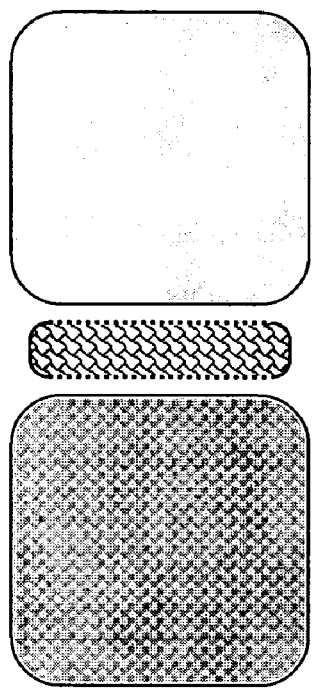
FIG. 1 is a cross-sectional view of a sac according to an embodiment of the present invention which has been implanted between two sections of the spine.

The present invention may be used to fuse any sections of the spine, such as vertebra or sections of vertebra. These sections of the spine can be located at any part of the spine, such as the lumbar spine or the cervical spine. In one embodiment, the invention can be used to fuse sections of the cervical spine. For patients with severe degenerative illnesses, the method can be used to treat multiple sections of the spine and thereby provide a measure of relief to the patient.

The sac will normally be implanted in the spine during a surgical procedure, such as during an arthroscopic or endoscopic procedure. Arthroscopic surgery is a minimally invasive surgical procedure in which a physical examination of the interior of a joint is performed using an arthroscope, a type of endoscope that is inserted into the joint through a small incision.

In contrast to traditional surgery in which the joint has to be opened up filly, endoscopic surgery generally requires only small incisions for the endoscope and for the surgical instruments. In certain surgical procedures, a single incision can be used for both the endoscope and the surgical instruments. This procedure reduces the recovery time of the patient and may increase the rate of surgical success due to reduced trauma to the connective tissue.

In the cervical spine, if fusion is desired, the standard of care is to harvest a bone graft or a disk from the patient, and to replace a damaged or deteriorating disc with the harvested bone or disk. The present invention can be used to increase the height of the segments and the discs and disc space of the spine, when such a procedure is desirable. The invention can also be used to support or rework or enlarge the neural foramina, openings between every two vertebrae where the nerve roots exit the spine to reach the rest of the body. The procedure allows for opening a window to replace or fuse segments of the spine in need of repair, and fusion of the segments containing the bone graft.

The peripheral sides of the sac have a height which is generally equal to the desired height or distance between the vertebra or bones to be fused. The surfaces of the sac define an interior volume which is intended to be filled with bone tissue or other substances before or during implantation in the spine of a patient.

The term "bone tissue" is meant to comprise bone chips, bone fragments, osteocytes, bone cement, cartilage chips, cartilage-forming material, or any other type of natural, bioengineered, or synthetic bone tissue, and combinations thereof. The bone growth tissue regenerates or facilitates regeneration of natural bone and the fusion of the sections of the spine. The bone tissue may also be one or more sections of bone extracted from another part of the body and which approximate the size of the sac. The bone tissue may be a single unitary element, or it may comprise a plurality of separate elements of the same or different composition which will be implanted in the body. The bone tissue will normally comprise living bone tissue to facilitate the fusion of the sections of the spine. A biocompatible glue may be used to bond the portions of the bone tissue to form a larger structure inside the sac.

In addition to bone tissue, the sac may comprise other elements which are biocompatible and which support or foster the growth of bone in or into the sac. For example, the sac may comprise an inorganic bone growth support substance. Such a support material is any substance which supports or assists the growth of bone tissue in or into the implant area. The bone growth support may comprise a filler material to reduce the amount of bone tissue required to fill the sac. In one embodiment of the invention, the bone growth support is calcium phosphate or hydroxyapatite. Such inert fillers are known in the art.

The sac may also further comprise a hydrogel, or a hydrogel-type substance, in addition to bone tissue. Hydrogels generally are cross-linked polymers which hydrate to absorb water and form solids having physical properties similar to those of gelatin or soft contact lenses. A sac containing such substance is usually nonporous on all surfaces is placed into the nuclear cavity of the disc and hydrates to expand and fill the cavity. In alternative embodiments, the sac may be slightly porous. The hydrogel is compressible and by this means, allows motion, much like a normal disc nucleus. The hydrogel may be in a hydrated condition or in an unhydrated condition when it is placed in the sac for implantation. Placement of a hydrogel implant within the disc space generally provides the lift that is necessary to restore and maintain disc space height in most patients.

In certain embodiments, a surgeon may choose to implant a sac according to the present invention which comprises a hydrogel and which does not contain bone tissue. In such an embodiment, the hydrogel may be hydrated before it is placed into the sac.

The sequence of the steps of the method is not critical, although it will depend upon the particular medical situation. For example, the sac may be placed in position between the sections of the spine to be fused, and then filled with bone tissue (or other substances). Alternatively, the sac may be first filled and then placed between the sections of the spine. In another embodiment, the sac may be partly filled, moved into position, and then filled with the bone tissue. The sac does not necessarily need to be completely filled with bone tissue. In such instances, the sac will normally be drawn around its interior contents and then closed and tightly sealed to obtain a non-leaking package.

The sac may be composed of a bio-resorbable or a non-bioresorbable material. When the sac is bio-resorbable, the sac is slowly biodegraded as bone tissue is regenerating in the area of implantation. Nevertheless, the sac has sufficient stability to maintain its shape without undergoing deterioration before fusion of the bone has been completed or before permanent stability has been obtained. If the sac is non-bio-resorbable, the sac generally remains in its original condition after implantation for an extended period of time, for example, for a year. Portions of the sac may also be bio-resorbable and other portions may be non-bio-resorbable. For example, the porous portions of the sac abutting bone may be bio-resorbable and the peripheral surfaces not abutting bone may be non-bio-resorbable.

The choice of sac size will depend upon individual circumstances, and different patients will require sacs of different sizes. The sac will generally be larger when a larger section of the spine must be fused, and smaller when smaller sections are to be fused. The decision to use a sac having a particular size can be can be made in advance if the surgeon is aware of the patient's particular needs. Alternatively, the decision of a particularly-sized sac can be made intraoperatively using measurements obtained during the surgery. In one embodiment, the sac has a diameter of about 12 mm, and a height of about 6-7 mm.

For example, prior to insertion of the sac, a guidewire or cannula of known length may be doubled over on top of itself and the double end inserted into a delivery tube into the area of the spine to be fused. The spinal area can be monitored using medical imaging. With knowledge of the length and width of the delivery tube, the length of the guidewire in the patient, and the appearance of the wire under imaging, the appropriate size for the circumference of the sac can be determined.

The shape of the sac will be chosen so as to fit in its intended area of implantation. In general, the surfaces of the sac and the existing bone will generally be flat in order to maximize apposition or contact between the surfaces. If the surfaces of the spine are not flat, these surfaces may be shaved or planed so as to make them planar prior to implantation, and to encourage growth and ingrowth of bone into the implant area. Alternatively, a surgeon may select a sac which has non-flat surfaces which complement or mate with the existing bone surfaces. The surfaces of the sac which contact bone are porous to permit bone ingrowth and fusion, and the surfaces not contacting bone are non-porous.

In one embodiment, the sac has the general appearance of a pill. In such an embodiment, the sac has flat top and bottom surfaces, and a peripheral surface between the upper and lower surfaces. The upper and lower surfaces of the sac may have a generally non-rectilinear, round, or oblate shape. In general, sharp vertices or points will be avoided to prevent pain or damage to existing bone. In general, the sac will have a round or oval overall shape.

The entire top and bottom surfaces of the sac do not necessarily have to be porous, and there can be portions of the surface which are non-porous. For example, if the diameter of the sac is larger than the adjoining bone, a central portion of the sac which will contact bone may be porous, and the rim portion of the sac which would not contact bone may be non-porous.

The sac may be formed from natural materials, synthetic materials, or a combination of both. Examples of materials of construction include metals such as titanium or tantalum, and polymers such as high density polyethylene and polyurethane. It will be obvious that the material chosen must be biocompatible to avoid rejection by the body, and such materials are known to those in the art.

The material chosen for the sac may be a woven or non-woven substance such as a fabric. For example, the sac may have porous woven upper and lower surfaces which are intended to abut existing bone, and a non-porous non-woven peripheral surface which would not abut bone tissue. The sac may also be formed from a unitary sheet of a material in which pores, holes or perforations have been made in the areas which are to abut bone in the spine. These perforations may be made using a punch or other such device. The sac may also be formed of two or more materials, such as a synthetic polymer interwoven with metallic threads or fibers.

The sac has an opening through which the bone tissue can be placed using any convenient means, such as a syringe, cannula, forceps, or other convenient means. The sac can be closed after filling using any convenient means, such as clips, sutures, staples, heat sealing, or other techniques known in the art.

The sac can be delivered to the area of implantation via a cannula, endoscope, or arthroscope, or using other delivery means. Cannulas and arthroscopes generally have a fairly narrow diameter in order to minimize tissue damage. For example, an arthroscope used for spinal surgery may have a diameter of about 4 mm. In order to fit the sac through an arthroscope or other narrow delivery tube, the sac may be collapsible or have a spring mechanism so that it can be folded upon itself prior to insertion. After delivery to the appropriate location in the body, the spring mechanism can be activated to expand the sac to its full shape for final installation/implantation and filling. The sac can be filled with its contents through the cannula or arthroscope, or using other means.

The sac may optionally comprise a rigid structural element for maintaining the sac in an expanded state upon filling. This structural element may be a band or wire which encircles the peripheral surface of the sac or runs circumferentially through the sac. The structural element may be present in the sac prior to implantation in the body, or it may be placed in the sac during the procedure.

The structural element is generally very flexible to permit facile insertion and movement during installation in the sac. The structural element may be placed in the sac via a delivery tube during the implantation procedure, or it may be already located in the sac prior to implantation. When the sac with the structural element is placed through the delivery tube, it may open in a predetermined manner so as to orient the sac in the proper position prior to insertion of bone tissue.

The structural element can be manufactured from any type of material, such as plastic or metal. The structural element may be pre-stressed so as to have a resiliency or memory effect to facilitate its proper placement in the sac or to expand the sac into the correct position or shape.

The rigid structural element may be opaque to medical imaging equipment. In such a manner, a surgeon implanting the sac in the spine can monitor the placement of the sac relative to existing bone or tissues using imaging techniques and thereby facilitate implantation. A non-exhaustive list of medical imaging techniques includes fluoroscopy, tomography, CAT scanning, magnetic resonance imaging, and ultrasound techniques.

The height of the sac generally corresponds to the distance between the sections of the spine to be fused in order to provide for maximal growth of bone. Alternatively, the height of the sac may be slightly or substantially larger than the distance between the sections of the spine so that the sections of the spine are moved apart, e.g. to lengthen or straighten the spine.

A radio-opaque wire or other structural element may be incorporated into the equator of the sac for documentation of placement for safety reasons or to monitor the occurrence of any migration of the sac which may occur.

Another aspect of the invention provides for a kit for fusing spinal bone. The kit comprises the sac according to the invention; and a device for filling the sac. This device may have any form which can transfer or transport bone tissue to the interior of the sac. In one embodiment, the device for filling the sac is a syringe or cannula which is known in the art. The device may be disposable or reusable.

The kit may be provided as a single sealed package, or the kit may be provided as separate components in a package. The kit may be provided in a sterilized or non-sterile condition. The sterilization may be performed using steam, ethylene oxide, radiation, or other convenient techniques known in the art.

The present invention will now be described with reference to the Figures which illustrate the general principles of the invention. FIG. 1 illustrates a cross-sectional view of an embodiment of a sac according to the present invention. The sac has been implanted schematically between two sections of the spine to be fused. The upper and lower surfaces of the sac (depicted using a dashed line) abut the existing spinal bone and comprise porous material. The porosity allows for bone to grow between the spine and the sac. The surfaces of the sac not abutting the sections of the spine are nonporous to bodily fluids and thereby prevent deterioration of the inserted bone tissue before the bone tissue has had a chance to regenerate.

Figure 2:
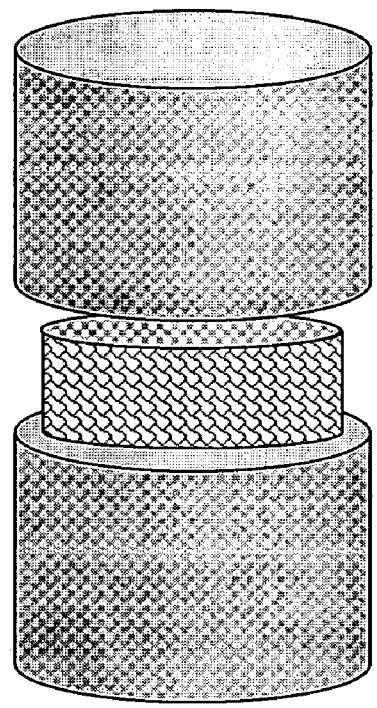
FIG. 2 is a three-dimensional perspective view of the embodiment illustrated in FIG. 1.

FIG. 2 is a three-dimensional perspective view of the embodiment illustrated in FIG. 1. FIG. 2 shows a sac according to an embodiment of the invention embedded into a portion of the spine of a patient. The surfaces of the sac abutting bone are porous and allow for bone ingrowth between the sac and the spine. The peripheral surface of the sac is non-porous to bodily fluids and thereby prevents deterioration of the bone tissue located in the sac.

For clarity of detail, FIGS. 1 and 2 show the sac as having a height which is slightly smaller than the distance between the bone to be fused. In use, the sac will nevertheless generally have the same height as the distance between the sections of the spine in order to have efficient fusion between the bone and bone tissue and to prevent inflow of bodily fluids. The height of the sac may also be larger than the distance between the sections of the spine so that the sections of the spine are moved apart during fusion.

Figure 3:
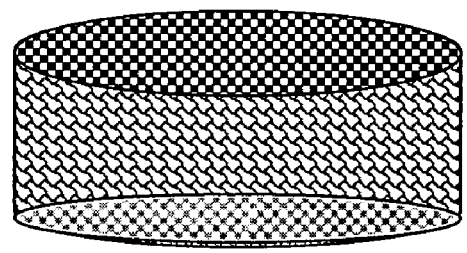
FIG. 3 illustrates a sac according to an embodiment of the present invention in the shape of a pill.

FIG. 3 illustrates a sac according to an embodiment of the present invention in the shape of a pill. The sac has porous upper and lower surfaces to allow for growth of bone between the sac and the section of the spine into which the sac is implanted. The sac also has non-porous peripheral surfaces to prevent bodily fluids from entering the sac.

While the invention has been particularly shown and described with reference to particular embodiments, those skilled in the art will understand that various changes in form and details may be made without departing from the spirit and scope of the invention.

What is claimed is:

1. A method for fusing spinal bone, the method comprising the steps of:
   (a) providing a collapsible sac having a unitary structure and generally flat upper and lower surfaces and a peripheral surface between the upper and lower surfaces, the surfaces defining an interior volume to be filled with bone tissue without leakage of the sac contents when filled, the upper and lower surfaces comprising porous material and the peripheral surface being nonporous to bodily fluids, the porous material for allowing bone to grow into and out of the upper and lower surfaces of the sac, and wherein the sac is free of structural walls affixed to the peripheral surface;

(b) delivering the sac in a collapsed state to the area of implantation in the spine; and (c) filling the sac to an expanded state with bone tissue.

2. The method according to claim 1, wherein the sections of the spine are vertebra.

3. The method according to claim 1, wherein the sections of the spine are sections of the lumbar spine, cervical spine, or both.

4. The method according to claim 1, wherein the bone tissue comprises bone chips, bone fragments, osteocytes, bone cement, cartilage chips, cartilage-forming material, or combinations thereof.

5. The method according to claim 1, wherein the sac further comprises an inorganic bone growth support.

6. The method according to claim 5, wherein the inorganic bone growth support is calcium phosphate.

7. The method according to claim 1, wherein the sac further comprises a hydrogel.

8. The method according to claim 1, wherein the sac is bio-resorbable or non-bioresorbable.

9. The method according to claim 1, wherein the sac has the general appearance of a pill.

10. The method according to claim 1, wherein the sac is formed from a synthetic material, a natural material, or both.

11. The method according to claim 1, wherein the sac further comprises a structural element for maintaining the sac in an expanded state upon filling.

12. The method according to claim 11, wherein the structural element is opaque to medical imaging equipment.

13. The method according to claim 1, wherein the surfaces of the sac abutting the sections of the spine are flat.

14. The method according to claim 1, wherein the height of the sac generally corresponds to the distance between the sections of the spine to be fused.

15. The method according to claim 1, wherein the method is performed during an endoscopic or arthroscopic surgery procedure.

16. A sac for fusing spinal bone, the sac having a unitary structure and lower surfaces and a peripheral surface between the upper and lower surfaces, the sac having a closed collapsible state for delivery to an implantation location, wherein the sac is folded upon itself, the sac having an opened expanded state when positioned at the implantation location, wherein the surfaces define an interior volume to be filled with bone tissue without leakage of sac contents when filled, the upper and lower surfaces of the sac comprising porous material for allowing bone to grow into and out of the interior volume when the sac is in the expanded state, and the peripheral surface is nonporous for preventing bodily fluids from entering the sac when the sac is in the expanded state, wherein the sac is free of structural walls affixed to the peripheral surface, and the sac is pre-sized and pre-shaped to fit complimentary within the implantation location.

17. The sac according to claim 16, wherein the spinal bone is a part of the cervical spine.

18. The sac according to claim 16, wherein the sac is structured for implantation into spinal bone during an arthroscopic or endoscopic procedure.

19. The sac according to claim 16, wherein the sac increases the height of segments of the spine, disks of the spine, or disc space of the spine.

20. The sac according to claim 16, wherein the peripheral sides of the sac have a height which is generally equal to the desired height or distance between vertebra or bones to be fused.

21. The sac according to claim 16, wherein the bone tissue is selected from the group consisting of bone chips, bone fragments, osteocytes, bone cement, cartilage chips, cartilage-forming material, natural bone, bioengineered bone, synthetic bone, and combinations thereof.

22. The sac according to claim 16, wherein the bone tissue is (a) a single unitary element; or (b) a plurality of separate elements of the same or different composition.

23. The sac according to claim 16, wherein the bone tissue comprises one or more substances selected from the group consisting of a biocompatible glue, an inorganic bone growth support substance, and a filler material.

24. The sac according to claim 16, wherein the sac is filled with a hydrogel instead of bone tissue.

25. The sac according to claim 16, wherein the sac is composed of a bio-resorbable material, a non-bioresorbable material, or both.

26. The sac according to claim 16, wherein the sac has a diameter of about 12 mm and a height of about 6-7 mm.

27. The sac according to claim 16, wherein the sac has a non-rectilinear, round, oblate, oval, or pill-like shape.

28. The sac according to claim 16, wherein the upper and lower surfaces of the sac comprise portions which are non-porous.

29. The sac according to claim 16, wherein the sac is formed from a woven or non-woven natural or synthetic material.

30. The sac according to claim 16, wherein the sac comprises a synthetic polymer interwoven with metallic fibers.

31. The sac according to claim 16, wherein the sac has upper and lower surfaces which mate with existing bone surfaces in the implantation location.

32. The sac according to claim 16, wherein the sac has an opening through which bone tissue can be placed, and wherein the opening is sealed after the sac has been filled.

33. The sac according to claim 16, wherein the sac comprises a spring mechanism which is activated to expand the sac to its full shape for final installation in the body.

34. The sac according to claim 16, wherein the sac comprises a structural element for maintaining the sac in the expanded state upon filling.

35. The sac according to claim 34, wherein the structural element is a band or wire which encircles the peripheral surface of the sac or runs circumferentially through the sac.

36. The sac according to claim 34, wherein the structural element is pre-stressed so as to have a memory effect to facilitate placement of the sac in the body or to expand the sac into a desired position or shape.

37. The sac according to claim 34, wherein the structural element is opaque to medical imaging.

38. The sac according to claim 16, further comprising a radio-opaque structural element located in the equator of the sac for monitoring the placement of the sac within the body.

39. A kit comprising:

(a) the sac according to claim 16; and (b) a device for filling the sac.

40. The kit according to claim 39, wherein the device for filling the sac is a disposable or reusable syringe or cannula.

41. The kit according to claim 39, further comprising bone tissue.

* * * * *

UNITED STATES PATENT AND TRADEMARK OFFICE
CERTIFICATE OF CORRECTION

PATENT NO. : 8,226,722 B2  Page 1 of 1
APPLICATION NO. : 11/450600
DATED : July 24, 2012
INVENTOR(S) : Francis Pflum It is certified that error appears in the above-identified patent and that said Letters Patent is hereby corrected as shown below:

Col. 7:
Line 42 (claim 16): Insert --and generally flat upper-- after --structure--.

Signed and Sealed this
Eighteenth Day of September, 2012

David J. Kappos
*Director of the United States Patent and Trademark Office*